United States Patent [19]

Nobuyoshi

[11] Patent Number: 5,106,363
[45] Date of Patent: Apr. 21, 1992

[54] BLOOD PERFUSION SYSTEM AND TUBE USED THEREIN

[75] Inventor: Masakiyo Nobuyoshi, Kitakyushu, Japan

[73] Assignee: Terumo Kabushiki Kaisha, Tokyo, Japan

[21] Appl. No.: 417,639

[22] Filed: Oct. 5, 1989

[30] Foreign Application Priority Data

Oct. 11, 1988 [JP] Japan .................. 63-255300

[51] Int. Cl.$^5$ ............................. A61M 37/00
[52] U.S. Cl. ........................ 604/4; 604/280; 606/194
[58] Field of Search ................... 604/4-6, 604/27, 40, 43, 96, 153, 8-10, 28, 30, 32, 280, 283; 606/192, 194; 128/656-658

[56] References Cited

U.S. PATENT DOCUMENTS

| 4,037,599 | 7/1977 | Raulerson ............... 604/4 X |
| 4,195,637 | 4/1980 | Grüntzig et al. . |
| 4,299,226 | 11/1981 | Banka ............... 606/194 X |
| 4,459,977 | 7/1984 | Pizon et al. ............... 604/8 X |
| 4,563,170 | 1/1986 | Aigner ............... 604/5 |
| 4,581,017 | 4/1986 | Sahota ............... 604/101 |
| 4,610,674 | 9/1986 | Suzuki et al. . |
| 4,666,426 | 5/1987 | Aigner ............... 604/5 |
| 4,714,460 | 12/1987 | Calderon ............... 604/28 |
| 4,776,837 | 10/1988 | Kopp ............... 604/4 |
| 4,820,261 | 4/1989 | Schmoll et al. ............... 604/5 |
| 4,820,271 | 4/1989 | Deutsch ............... 604/99 |
| 4,828,543 | 5/1989 | Weiss et al. ............... 604/4 |
| 4,850,998 | 7/1989 | Schoendorfer ............... 604/28 |
| 4,867,742 | 9/1989 | Calderon ............... 604/28 |
| 4,883,459 | 11/1989 | Calderon ............... 604/28 |

FOREIGN PATENT DOCUMENTS

| 0148131 | 10/1985 | European Pat. Off. ............... 604/4 |
| 0174577A3 | 3/1986 | European Pat. Off. . |
| WO88/06465 | 9/1988 | European Pat. Off. . |
| 54-70683 | 6/1979 | Japan . |
| 61-71065 | 4/1986 | Japan . |
| WO88/06045 | 8/1988 | PCT Int'l Appl. . |
| WO89/08471 | 9/1989 | PCT Int'l Appl. . |

Primary Examiner—John D. Yasko
Assistant Examiner—Adam J. Cermak
Attorney, Agent, or Firm—Frishauf, Holtz, Goodman & Woodward

[57] ABSTRACT

In a blood perfusion system comprising a dilation catheter defining a lumen and including a dilating member at the leading end, and a sheath defining a bore through which the dilation catheter is inserted to define a blood intake gap between the outer surface of the dilation catheter and the sheath bore and including a transverse bore branched from the sheath bore, a tube is connected at one end to the transverse bore and at another end to the lumen of the dilation catheter at a trailing end. When the sheath having the dilation catheter inserted therein is set in a blood vessel, a pump in the tube operates to take blood into the blood intake gap in the sheath, pass through the tube and the dilation catheter lumen, and feed back to the periphery of a lesion through the open leading end of the dilation catheter. The patient's own fresh blood can be injected without the need for a further cutdown or puncture for blood intake.

15 Claims, 6 Drawing Sheets

BLOOD PERFUSION SYSTEM AND TUBE USED THEREIN

BACKGROUND OF THE INVENTION

1. Field of the Invention

This invention relates to a blood perfusion system for percutaneous transluminal angioplasty to, for example, femoral and coronary arteries for the purpose of dilating the stenosis to improve blood flow therethrough. It also relates to tube means used in such a blood perfusion system.

2. Prior Art

In treating a stenosis in a vessel such as coronary artery, a dilation catheter having a balloon at a distal region thereof is inserted into the vessel until the balloon reaches the lesion. The balloon is then inflated to expand the stenosis. The inflated balloon inevitably blocks the relevant portion of the vessel to stop further blood flow. Continued blood flow interruption for some time is dangerous to the patient. Thus, if the operation takes a long time, it is critical to ensure normal blood flow by transporting a necessary amount of blood to the periphery of the lesion through the lumen of the dilation catheter.

The following two methods are known for such blood perfusion.

A first method is to previously collect blood in a blood bag from the patient herself or himself or another person. During the operation, the blood in storage is introduced into the lumen of the dilation catheter and injected to the periphery of the lesion.

A second method is to aspirate blood from another vessel of the patient under operation. The blood taken in is directly fed to the lumen of the dilation catheter and injected to the periphery of the lesion over the entire operation period.

However, the first method has a problem that the blood feed which has been in storage is less fresh and can cause infection. A problem of compatibility with the patient arises particularly when blood from another person is used.

The second method is advantageous in that fresh blood can be fed. Nevertheless, in addition to the site where the dilation catheter is inserted or the sheath is indwelled in the patient's vessel, a cutdown or puncture must be done at another site of the vessel (for example, a blood intake needle be punctured) for the purpose of aspirating blood. This adds to the burden to the patient. The additional burden is serious to old patients, the majority of patients who need a treatment to dilate a stenosis.

SUMMARY OF THE INVENTION

Therefore, an object of the present invention is to eliminate the above-mentioned problems and to provide a novel and improved blood perfusion system which can perfuse fresh blood of the patient herself or himself through the vessel across a lesion during operation without making an additional cutdown or puncture for blood intake, thereby imposing no additional burden to the patient.

Another object of the invention is to provide tube means for use in such a blood perfusion system.

According to the present invention, there is provided a blood perfusion system comprising a dilation catheter, a sheath, a tube, and a pump. The dilation catheter has leading and trailing ends and defines a longitudinal lumen extending from the leading end to the trailing end and open at the leading and trailing ends. The dilation catheter further includes a dilating member at the leading end. The sheath has leading and trailing ends and defines a longitudinal bore through which the dilation catheter is insertable. When the dilation catheter is inserted therein, the sheath defines a blood intake gap between the outer surface of the dilation catheter and the sheath bore. The sheath further includes transverse bore means in fluid communication with the sheath bore. The tube means for defining a continuous flowpath is connected at one end to the transverse bore means and at another end to the trailing end of the lumen of the dilation catheter. The pump means is mounted in the tube means for pumping blood. When the sheath having the dilation catheter inserted therein is set in a blood vessel, blood is taken into the blood intake gap in the sheath, passed through the sheath bore, the tube means, and the dilation catheter lumen, and fed back to the vessel through the open leading end of the dilation catheter.

Further, a guiding catheter having a lumen through which the dilation catheter is insertable may be provided. In this case, the guiding catheter with the dilation catheter received therein is inserted in the sheath.

In a preferred embodiment, the system may further include means inserted in the flowpath of said tube means for storing blood.

The sheath may further include a valve body mounted at the trailing end thereof for blocking the sheath bore when the sheath bore is empty and sealing any gap when the dilating or guiding catheter is inserted therein.

In another aspect, the present invention provides tube means for defining a continuous flowpath having one end connectable to the transverse bore means and another end connectable to the trailing end of the lumen of the dilation catheter, the tube means including at least one section of tubing to which blood pumping means is mountable.

According to the present invention, a gap for blood intake is defined between the bore of the sheath to be endermically indwelled in the vessel and the dilation catheter. During an operation, blood is taken in through the intake gap, passed through the sheath bore, the tube means or blood feed circuit connected to the sheath bore, and the lumen of the dilation catheter connected to the circuit, and fed back to the vessel through the leading opening of the dilation catheter. Since blood is taken into the intake gap through the leading end of the sheath endermically indwelled in the patient's vessel, it is unnecessary to make a cutdown or puncture at another site of the vessel, mitigating a burden to the patient.

The operation may be carried out as described above in the case of a relatively thick vessel such as femoral artery. In the case of a relatively thin vessel such as coronary artery, a guiding catheter may preferably be used.

BRIEF DESCRIPTION OF THE DRAWINGS

The above and other objects, features, and advantages of the present invention will be better understood from the following description taken in conjunction with the accompanying drawings, in which.

Like parts are designated by the same reference numerals throughout the figures.

DESCRIPTION OF THE PREFERRED EMBODIMENTS

Figure 1:
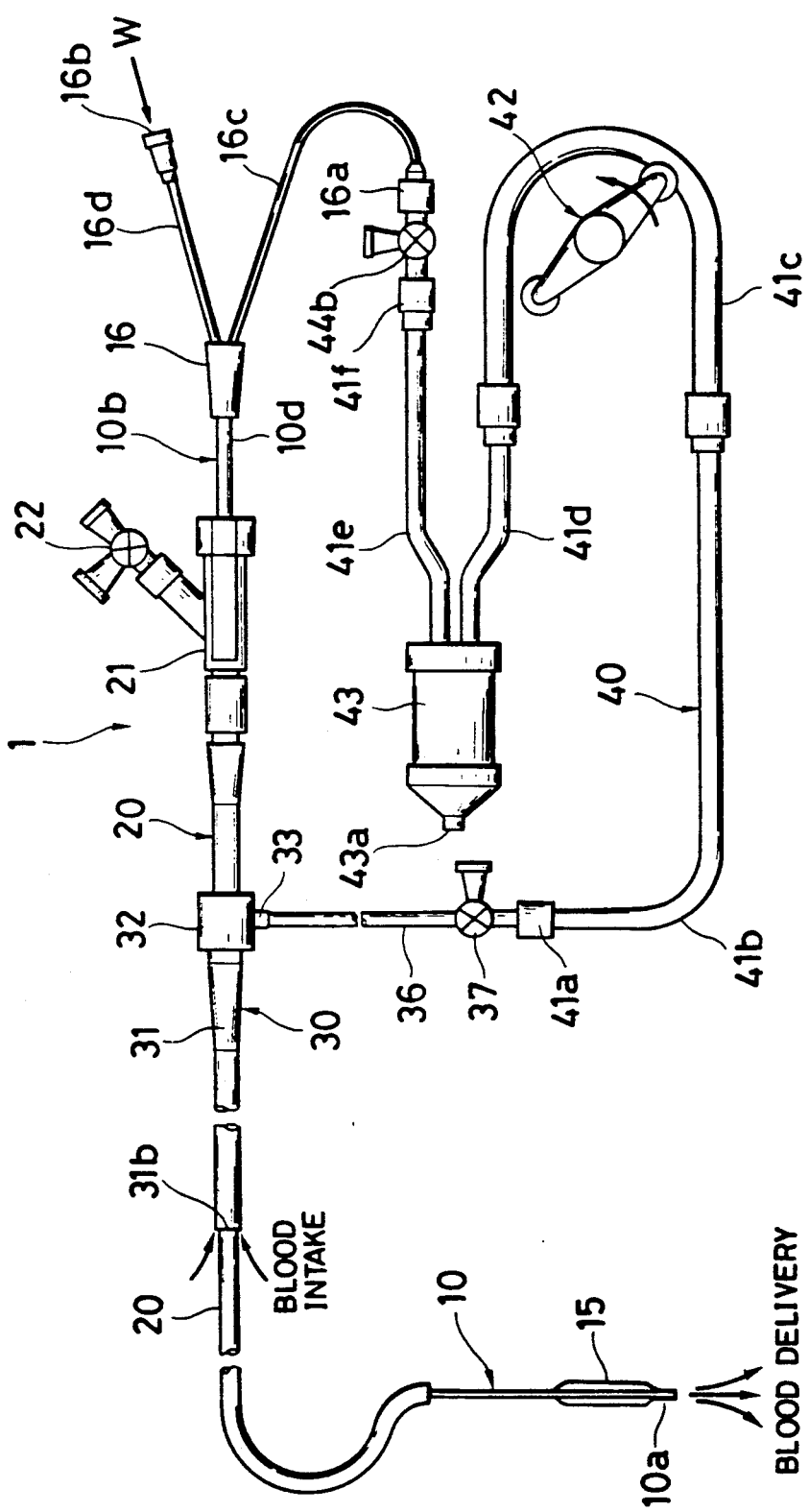
FIG. 1 is a schematic illustration of a blood perfusion system according to one embodiment of the invention, the system, including a dilation catheter, a guiding catheter, a sheath, and tube means.

The blood perfusion system of the present invention and the tube means used therein are now described in further detail by referring to their embodiments shown in the figures.

Although the blood perfusion system of the present invention is illustrated herein as being applied to the coronary artery, its application is not limited thereto. Further in the disclosure, the terms "leading end" and "trailing end" are generally used in connection with catheters and associated members on a basis of the direction of inserting the catheter into a vessel during an operation. The terms "lumen" and "bore" have an interchangeable meaning of the cavity of a tubular member. Reference numeral 2 designates a blood vessel under operation and 3 designates a stenosis or lesion.

FIG. 1 is a schematic illustration of one embodiment of a blood perfusion system according to the present invention. Briefly stated, the blood perfusion system generally designated at 1 includes a dilation catheter 10, a guiding catheter 20, a sheath 30, and tube means or blood pumping circuit 40. It will be understood from the following description, the guiding catheter is optional.

Figure 2:
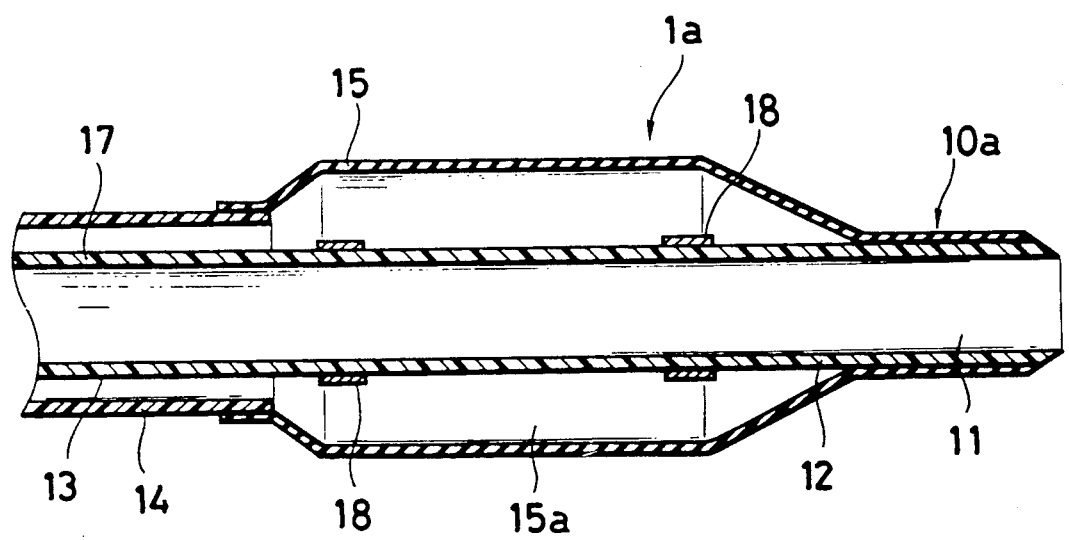
FIG. 2 is an enlarged longitudinal cross section of a leading portion of the dilation catheter used in the system of FIG. 1.

The dilation catheter 10 is first described. FIGS. 2 and 3 are enlarged axial cross-sections of leading and trailing portions of the dilation catheter used in the blood perfusion system of FIG. 1. The dilation catheter 10 is mainly composed of an elongated flexible tubular section of the double wall structure which includes an inner tube 12 defining a first longitudinal bore or lumen 11 therethrough and an outer tube 14 defining a second longitudinal bore or lumen 13 therethrough coaxially surrounding the inner tube 12 to leave an annular space therebetween. The dilation catheter 10 further includes a dilating member 15 attached to a leading portion 10a of catheter 10 and a branch hub 16 of generally Y shape attached to a trailing portion 10a of catheter 10. The catheter 10 is of a fluid tight structure as a whole.

The first lumen 11 of inner tube 12 extends from the leading end 10a to the trailing end 10b of dilation catheter 10. The first lumen 11 is open at its leading end in a forward direction and communicates at its trailing end with a first opening 16a of branch hub 16.

The second lumen 13 of the outer tube 14 also extends from the leading end 10a to the trailing end 10b of dilation catheter 10, and communicates at its leading end with an interior space 15a of dilating member 15 and at its trailing end with a second opening 16b of branch hub 16.

It is to be noted that the dilation catheter 10 is not limited to the double tube structure of the illustrated embodiment and may take a double lumen structure wherein two lumens extend in juxtaposition or a double tube structure combined with a double lumen structure.

The inner tube 12 is preferably formed from a synthetic resin material having a rigidity imparting member 17, for example, tubular metal mesh integrally embedded therein so that the inner tube undergoes no twisting or bending when rotating forces are applied thereto by a guiding catheter 20 as will be described later.

Also preferably, a length of metallic wire may be inserted and fixedly indwelled in the second lumen 13 between the inner and outer tubes 12 and 14 so that the wire extends from the leading end to the trailing end of the lumen because the indwelling wire assists in inserting of the catheter.

The outer surface portion of the inner tube 12 where it is surrounded by the dilating member 15 is preferably provided at two axially spaced positions, for example, with marks 18 of radiopaque material having any desired shape in order that the location of the dilating member 15 can be visually identified under fluoroscopic observation.

The dilating member 15 may be formed of resinous material such as polyethylene terephthalate (PET), polyvinyl chloride (PVC), and ethylene-vinyl acetate copolymer (EVA). The dilating member 15 has a forward end attached to the outer surface of the inner tube 12 leading portion and a rear end attached to the outer surface of the outer tube 14 leading portion as by adhesive bonding or fusion welding.

Figure 3A:
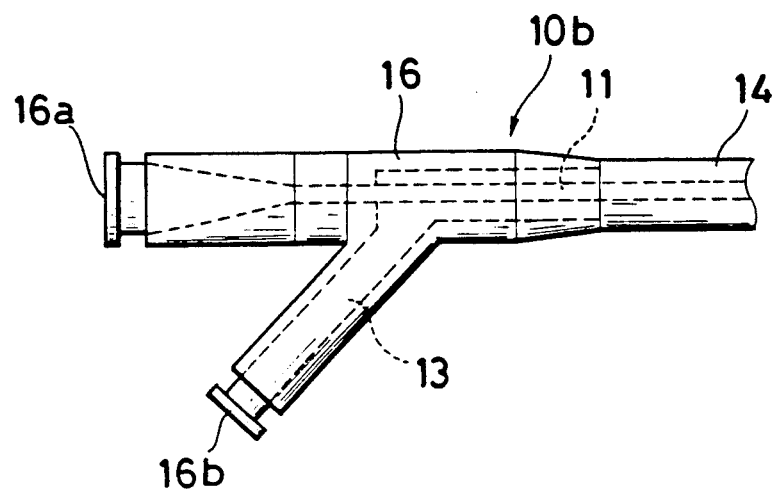
FIGS. 3a and 3b illustrate different examples of a trailing portion of the dilation catheter used in the system of FIG. 1.

The branch hub 16 is configured in Y shape having the first opening 16a at one branch and the second opening 16b the other branch as shown in FIG. 3a. A flexible guide wire G (see FIGS. 8 and 9) is inserted into the first opening 16a of branch hub 16 when it is desired to insert the dilation catheter 10 to the stenosis 3 in the vessel 2. The second opening 16b of branch hub 16 is connectable to an admission line for dilating fluid W when it is desired to introduce the dilating fluid into the dilating member 15.

Figure 3B:
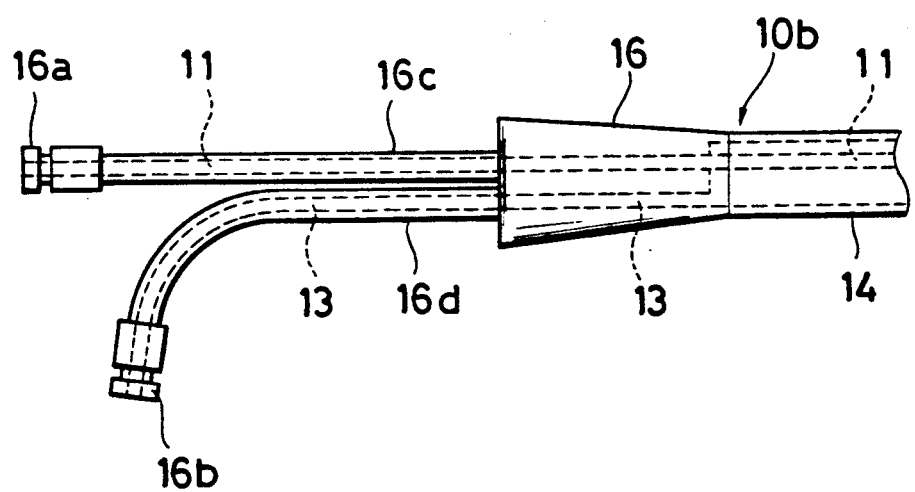

Alternatively, as shown in FIG. 3b, the branch hub 16 may also be composed of a sleeve and flexible connecting tubes 16c and 16d extending from the sleeve and terminating at free ends to which the first and second connectors 16a and 16b are attached.

The dilation catheter 10 of the above-illustrated construction is inserted through a guiding catheter 20. Upon insertion, the leading end portion 10a leads the catheter 10.

Figure 4:
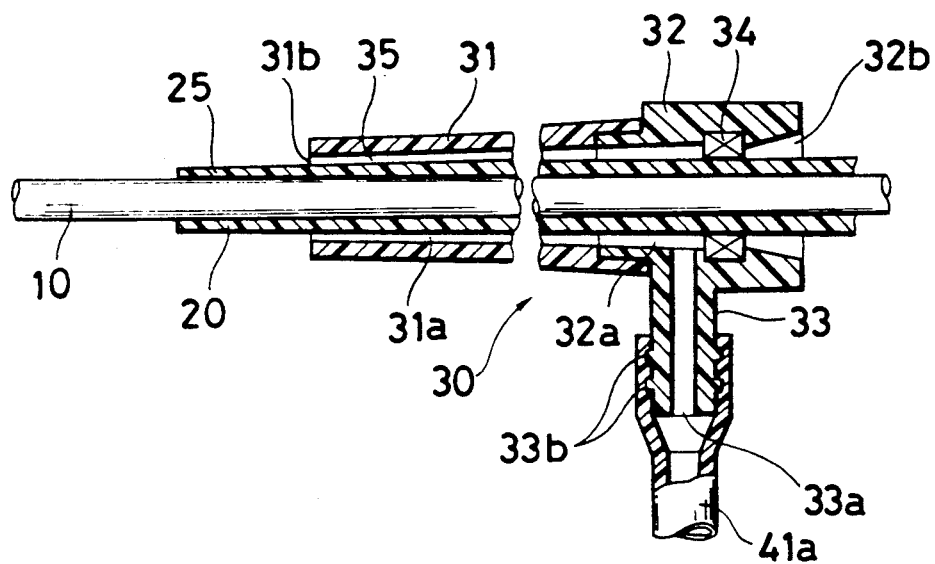
FIG. 4 is an enlarged, partially short cut, longitudinal cross section of the sheath used in the system of FIG. 1.

As shown in FIG. 4, the guiding catheter 20 is a tubular member defining a lumen 25 adapted to receive either a guide wire (not shown) which serves to lead the guiding catheter 20 when it is directed to a predetermined site in the vessel or the dilation catheter 10.

In carrying out an operation for dilating the stenosis 3, the guiding catheter 20 is received for longitudinal motion and rotation in a sheath 30 to be described later. The guide wire (not shown) is inserted into the lumen 25 of guiding catheter 20, if desired, through a rotary connector 21. After the leading end of the guiding catheter 20 has reached a predetermined position, the guide wire is withdrawn. Instead, a contrast medium is injected for angiography.

As described above, the dilation catheter 10 or guide wire G is introduced into the lumen 25 of guiding catheter 20 through the rotary connector 21. The rotary connector 21 defines a main bore through which the dilation catheter 10 is inserted. The connector 21 is preferably provided with a branch having a three-way cock 22 or a multi-port manifold which is used when it is desired to carry out another action (for example, contrast medium injection or blood pressure measurement) during the operation.

FIG. 4 illustrates a cross-sectional structure of the sheath 30. As seen from the figure, the sheath 30 is an elongated, generally cylindrical member defining a longitudinal lumen or bore 35 and having leading and trailing ends. The sheath 30 includes a generally cylindrical sheath body 31 formed of a fluoro-resin material such as ethylene tetrafluoroethylene (ETFE), perfluoroalkoxyl (PFA) resin, and fluorinated ethylene propylene (FEP) and a hub 32 of metal or rigid synthetic resin fluid-tightly engaged with a trailing portion of sheath body 31, and a transverse protrusion 33 extending from at least one lateral site on the hub 32 for connection to a blood feed circuit 40 which will be described later. The transverse protrusion 33 is connected to a three-way cock 37 through a sheath or side tube 36 as shown in FIG. 1. A valve body 34 to be described later is mounted in the bore of hub 32 at its inlet portion 32b.

The guiding catheter 20 is loosely received in the bore 35 of sheath body 31 to define a gap 31a for blood intake between the inner surface of bore 35 and the outer surface of guiding catheter 20. The sheath body 31 is dimensioned such that the inner diameter of sheath body bore 35 is larger than the outer diameter of guiding catheter 20. The dimensions of these members dictate the cross-sectional area of the gap or flowpath 31a for blood intake and are selected so as to ensure that blood enters the gap 31a at the maximum necessary flow rate through a blood intake opening 31b at the leading end of sheath body 31 when the sheath 30 is set in the brachial or femoral vessel 2. The necessary flow rate of blood may vary with a disease case (the extent of treatment, the type and thickness of a particular vessel to be endermically reached, for example) and is desirably in the range of about 40 to 50 ml/min. in the case of coronary artery operation.

The hub 32 defines a bore 32a of an approximately equal diameter to that of sheath body bore 35 in fluid communication with the blood intake gap 31a. The hub bore 32a at a trailing end is diverged to form the inlet portion 32b through which the guiding catheter 20 is inserted.

The transverse protrusion 33 on the side of hub 32 for connection to the blood feed circuit 40 defines a transversely extending bore 33a which is in fluid communication with the blood intake gap 31a through the hub bore 32a. Since the sheath tube 36 is fitted over the protrusion 33, the protrusion 33 is preferably formed on the outer surface with engaging ribs 33b for preventing accidental disengagement of the tube 36 therefrom.

The valve 34 is generally mounted in the hub 32 for the purpose of preventing the blood which has entered the bore 35 through the blood intake opening 31b from flowing to the exterior through the inlet portion 32a when the sheath 30 is dwelled in the vessel, but the guiding catheter 20 is not inserted in the sheath bore 35. The valve 34 also plays the role of preventing air from entering the hub bore 32a from the exterior when the guiding catheter 20 having the dilation catheter 10 inserted therein is inserted into the sheath bore 35.

Figure 5:
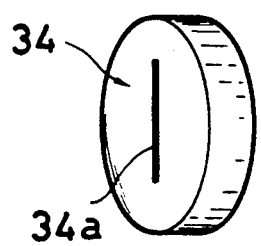
FIGS. 5 and 6 are perspective views of the valve body mounted in the sheath of FIG. 4, FIG. 5 showing the outer configuration and FIG. 6 being a see-through view showing the internal structure of the valve body.
Figure 6:
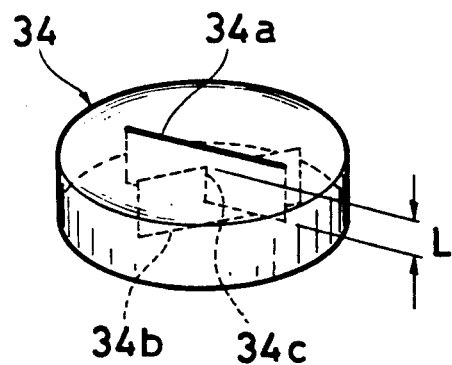

The valve body 34 may be a solid cylindrical disk having a pair of opposed circular surfaces as shown in FIGS. 5 and 6. The cylindrical valve body has a first slit 34a open only on one circular surface and a second slit 34b open only on the other circular surface, both slits 34a and 34b axially extending a portion of the entire axial length of the valve body. Within the valve body the slits 34a and 34b cross each other along an intersection 34c having an axial length L. The valve body 34 is formed from a resilient material such as various rubbers and elastomeric resins. When the guiding catheter 20 is inserted into the valve body 34, the valve body 34 makes a continuous surface contact with the outer surface of the guiding catheter 20 from all directions in tight fit relation depending on the outer diameter of the guiding catheter 20, maintaining a fluid-tight seal between the sheath 30 and the guiding catheter 20.

Instead of the sheath 30 of the illustrated configuration, there may be used a sheath of the configuration disclosed in FIG. 2 of U.S. Pat. No. 4,610,674, which also discloses the detailed construction of the valve body 34 available in the present invention.

The tube means 40 which constitutes one of the features of the present invention provides a blood feed circuit having a function of pumping blood from the blood intake gap 31a to the first lumen 11 through the first opening 16a of branch hub 16. As shown in FIG. 1, the tube means 40 constitutes an essential portion of the blood perfusion circuit of the blood perfusion system 1 and basically includes a first connector 41a, a plurality of serially connected sections of tubing 41b, 41c, 41d, and 41e, and a second connector 41f.

The tube means 40 has one end connected to the three way cock 37 at the free or downstream end of the sheath tube 36 through the first connector 41a and another end connected to the first opening 16a at the leading end of the connecting tube 16c extending from the branch hub 16 through the second connector 41f. Preferably, a three-way cock 44b is interposed between the second connector 41f and the first opening 16a because the cock enables admission of medicament, blood sampling, or pressure measurement upon blood pumping.

The sections of tubing 41b to 41e are usually formed from flexible or elastic material such as polyvinyl chloride, polyurethane, nylon, polyethylene (PE), ethylenevinyl acetate copolymer (EVA), and silicone. The sections of tubing preferably have an anti-thrombotic agent such as methyltrimethoxysilane coated on the inner surface thereof.

The tube means 40 further includes blood pumping means in the form of a pump 42 and a blood reservoir 43 at suitable locations along the line. Optionally, the tube means 40 may further include at least one three-way cock 44b as illustrated above. The first section of tubing 41b is connected to the sheath tube 36 through the first connector 41a and the cock 37 and to the pumping section of tubing 41c which is associated with the pump 42. The inlet section of tubing 41d connects the pumping section 41c to an inlet of the reservoir 43. The outlet section of tubing 41e extends from an outlet of the reservoir 43.

The blood pump 42 may be a roller pump commonly used in the medical field as shown in FIG. 1 because of its stable flow rate. The roller pump 42 is generally of a structure including an arm and a pair of cylindrical rollers pivoted for free rotation at opposite ends of the arm. As the arm is rotated at a certain revolution counter-clockwise as shown by an arrow in FIG. 1, alternate one of the two rollers makes a continuous contact with a semi-circular portion of the section of tubing 41c to squeeze the tubing from the beginning to the end, thereby feeding the blood in the tubing forward in a pulsative manner. The flow rate of blood may vary with a disease case (the extent of treatment, the type and thickness of a particular vessel under operation, for example) and is desirably in the range of about 40 to 50 ml/min. in the case of coronary artery operation. Such a flow rate can be controlled by the discharge capacity of the pump 42 which is, in turn, determined by the revolution of the arm and the inner diameter of the semi-circular section of tubing 41c.

The blood reservoir 43 is provided mainly for the purpose of removing bubbles from the blood. Since the operation of pump 42 produces a negative pressure in the bore 32a of sheath 30, some air can be sucked into the blood inflow through the valve body 34 if the fluid blocking function of the valve body 34 is incomplete. Since the presence of even a trace of air bubbles in the blood feed can cause a danger to the patient in the case of arterial operation, bubbles should be completely removed from the blood feed. The blood reservoir 43 is illustrated in FIG. 1 as if it lay horizontally. At least during service, the blood reservoir 43 has to stand straight such that its vent 43a is at the top. The vent 43a of blood reservoir 43 is preferably equipped with a two or three-way cock though not shown.

The three-way cocks 37 and 44b are provided for various purposes including admission of various medicaments including a contrast medium into the vessel 2, blood sampling, and blood pressure measurement as previously described.

Now, the operation of the blood perfusion system 1 of the above-illustrated construction is described.

(a) Before an operation for dilating the stenosis 3 formed in the vessel 2 is practiced, the dilation catheter 10 is removed of as much air as possible. To this end, suction or infusion means, most often a syringe filled with a fluid such as a contrast medium is connected to the second opening 16b of branch hub 16, for example. By actuating the syringe, the air in the second lumen 13 and the dilating member 15 is purged with the fluid from the syringe.

Figure 7:
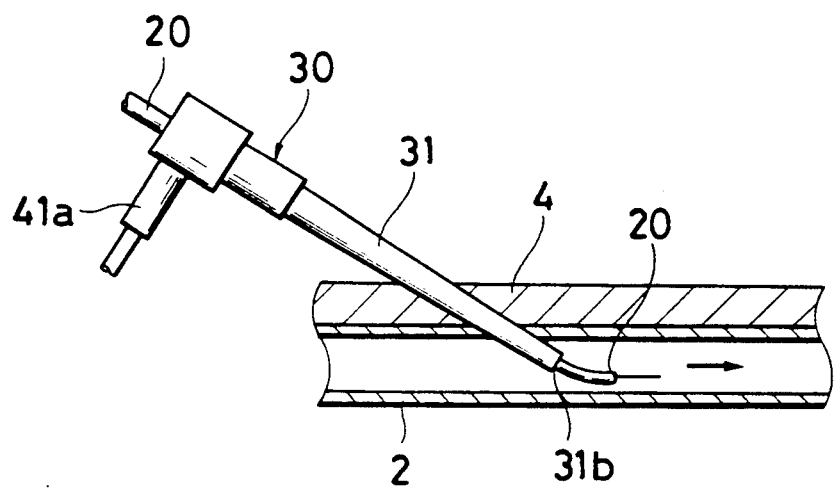
FIGS. 7 to 10 illustrate successive steps of operation using the blood perfusion system of the invention, FIG. 7 being a fragmental cross section showing the sheath inserted in the vessel, FIG. 8 being a fragmental cross section showing the dilation catheter inserted into the stenosis, FIG. 9 being a fragmental cross section similar to FIG. 8, but showing that the dilating member of the dilation catheter is inflated, and FIG. 10 being a fragmental cross section showing the dilation catheter through which blood is fed to the periphery of the stenosis.

The leading end portion of the sheath 30 is inserted into the vessel 2 of the patient lying on a bed of fluoroscopic equipment (not shown) through a puncture area 4 and indwelled thereat as shown in FIG. 7. At this point, the blood intake opening 31b of sheath body 31 is located within the vessel 2.

(c) After the sheath 30 is properly secured to the puncture area 4, the guiding catheter 20 having a guide wire previously inserted in its lumen 25 is inserted into the bore 35 of the sheath 30. The guiding catheter 20 is then introduced into the vessel 2 until it reaches a predetermined site while the guide wire leads the guiding catheter 20 during the process. The guide wire is then withdrawn. A contrast medium is injected into the vessel 2 through the guiding catheter 20 to identify the location of the stenosis 3 by fluoroscopy.

(d) After the location of the stenosis 3 is identified by fluoroscopy, the dilation catheter 10 having a guide wire G previously inserted therein is slowly inserted into the lumen 25 through the rotary connector 21.

Figure 8:
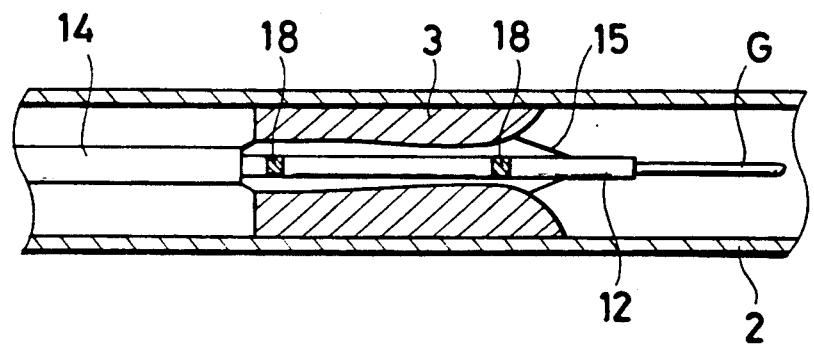

(e) The dilation catheter 10 is inserted until it reaches the leading end of the guiding catheter 20. Then the guide wire G in the first lumen 11 of dilation catheter 10 is manipulated so as to pass over the stenosis 3, and the dilation catheter 10 is moved forward along the guide wire G. As a result, the leading portion 10a of dilation catheter 10 is positioned in the stenosis 3 as shown in FIG. 8.

At this point, the radiopaque marks 18 applied to the inner tube 2 of dilation catheter 10 may be utilized to locate the dilating member 15 in registry with the stenosis 3 as the operator desires.

Figure 9:
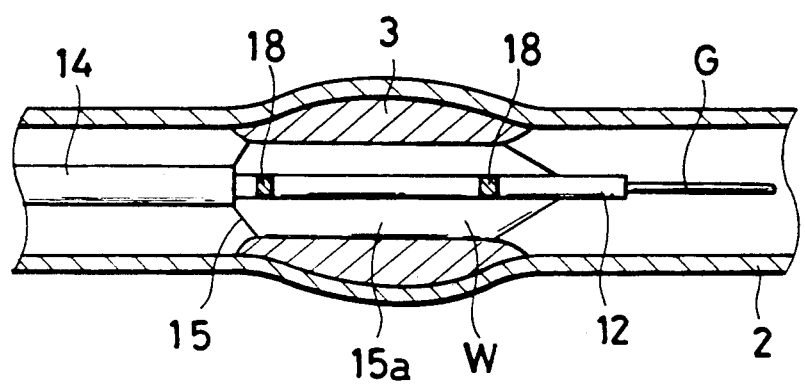

(f) After the leading portion 10a of dilation catheter 10 is settled in place, a dilating fluid W such as a contrast medium may be injected into the dilating member 15 through the second opening 16b of branch hub 16 to expand the interior space 15a of dilating member 15 as shown in FIG. 9. Then the stenosis 3 is dilated for improved blood flow.

After the dilating procedure is completed, the dilating fluid W is sucked out of the dilating member 15, allowing the dilating member to contract. The guide wire G is withdrawn from the first lumen 11. The situation is ready for blood delivery to the periphery of the stenosis 3.

(g) The interior of the tube means 40 is previously purged with saline or the like. The upstream end of the tube means 40 is connected to the sheath 30 through the three-way cock 37. The pump 42 is now actuated to take in blood. The pump 42 is stopped at the time when the interior of the tube means 40 is almost purged with blood.

Then the downstream end of the tube means or blood feed circuit 40 is connected to the first opening 16a of dilation catheter 10 from which the guide wire G has been withdrawn. The dilating member 15 of dilation catheter 10 is expanded before the pump 42 is actuated again.

(h) After the start of the pump 42, its pumping action creates a negative pressure in a circuit portion extending from the blood intake gap 31 of sheath 30 to the pumping tube section 41c of the series of tubing sections 41. The negative pressure causes the blood in the vessel 2 where the sheath 30 is indwelled to enter the intake gap 31a through the intake opening 31b and then reach the reservoir 43 through a route of sheath bore 32a→ transverse protrusion bore 33a→sheath tube 36→three-way cock 37→tube section 41b→pumping tube section 41c→inlet tube section 41d.

Since the negative pressure is created in the bore 32a of sheath 30, there is a possibility that a trace of air is introduced into the bore 32a to form bubbles in the blood through any interstice between the outer surface of guiding catheter 20 and the slits 34a, 34b of valve body 34. However, such bubbles entrained in blood are separated from the blood in the reservoir 43 and discharged through the vent 43 if desired. Therefore, the arrangement ensures that no bubbles harmful to the patient are present in the blood outflow from the reservoir 43 to the outlet section of tubing 41e.

If blood having bubbles entrained therein were pumped into the vessel 2, such bubbles would form thrombi in capillaries in various organs including the brain, causing cerebropathy after the operation. It is therefore essential to pay full attention to debubbling or air removal when arterial or similar operation is to be performed.

(i) During the operation of the pump 42, the fresh blood which is taken in from the patient herself or himself through the intake opening 31b and debubbled in the reservoir 43 is continuously pumped into the first lumen 11 of dilation catheter 10 through a route of reservoir 43→ outlet tube section 41e→three-way cock 44b→first opening 16a→tube 16c→branch hub 16.

Figure 10:
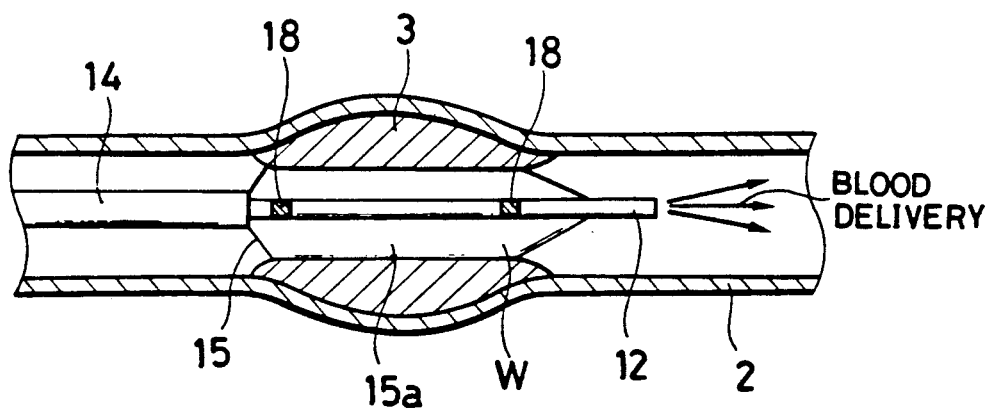

The blood is injected to the periphery of the stenosis 3 (that is, to a distal side of the vessel) through the leading opening of the first lumen 11 of inner tube 12 as shown in FIG. 10. This establishes a normal flow of the patient's own fresh blood.

CLINICAL EXAMPLE

A clinical example is given below in which a patient is treated using the blood perfusion system 1 of the above-illustrated arrangement.
Case: male (56 years old)
Site: LAD (left anterior descending artery), seg. 6

PROCEDURE (1) First, a dilation catheter Profile Plus (trade name of USCI) having a dilating member of 3 mm in diameter was used to dilate the stenosis under a pressure of 120 psi for one minute. The catheter was then contracted. It was found that an ST-segment on an electrocardiogram rose 5 mm over a period of 30 seconds.

(2) To smooth the inner side of the dilated portion, the blood perfusion circuit 1 of the illustrated embodiment which has been primed with saline was connected to the dilation catheter. The dilation catheter was dilated under a pressure of 60 psi. The pump in the circuit is operated so as to provide a presumed flow rate of about 30 ml/min. whereby the circuit was purged with the blood taken in from the patient herself or himself.

(3) The lesion was dilated for 3 minutes under the conditions. The blood perfusion circuit of the invention performed such that the ST-segment experienced no change for the first one minute and rose 3 or 4 mm during the subsequent two minutes. At the end of dilating operation the ST-segment resumed the original value.

(4) During the operation, no entry of air into the sheath 30 was recognized upon perfusion of blood taken in from the patient. The valve body 34 was found to exert a satisfactory air blocking function. No significant thrombus deposition was found throughout the circuit.

In this clinical example, methyltrimethoxysilane had been coated throughout the circuit in order to prevent thrombus deposition.

The clinical results show that with the use of the blood perfusion system of the invention, the blood taken in from the patient can be perfused to the periphery of a stenosis therein without undesirable entrainment of air while controlling the rise of ST-segment to about 3 to 4 mm for a period of 3 minutes.

As understood from the foregoing description, the blood perfusion system of the invention has several benefits.

(1) It reduces a burden to the patient by eliminating the need for another cutdown or puncture to the body.

(2) It prevents occurrence of any complication or sequela due to blood infusion during an operation because the patient's own fresh blood can be perfused in a real time manner during the operation.

(3) The gas blocking function of the valve body combined with the debubbling function of the blood reservoir prevents entry of air into blood feed, thus preventing occurrence of any complication due to an operation.

(4) The operator can perform an operation according to the conventional practice without any embarrassment because the respective steps and sequence thereof for manipulating the blood perfusion system of the invention are little changed from the steps and sequence commonly taken in a operation for a similar purpose.

Although the preferred embodiments of the present invention have been described, the invention is not limited thereto. Many modifications and variations may be made to the embodiments without departing from the scope of the invention.

More particularly, the dilation catheter for use in the blood perfusion system of the invention is not limited to the illustrated embodiment. For example, use may be made of dilation catheters of the Gruntzig type disclosed in U.S. Pat. No. 4,195,637 and the Simpson-Robert type disclosed in U.S. Pat. No. 4,323,071. In addition, a dilation catheter of the illustrated structure, but having a non-rigid inner tube may also be used.

There have been described the tube means and blood perfusion system of the invention wherein the patient's own fresh blood can be perfused during an operation by taking in blood from a vessel through the leading end of the sheath which is set in the vessel for allowing the dilation catheter to be inserted, passing the blood to the lumen of the dilation catheter through the tube means or blood feed circuit, and feeding back the blood to the periphery of the lesion through the leading opening of the dilation catheter, thereby avoiding an additional cutdown or puncture to another vessel for blood intake and thus adding no burden to the patient than necessary.

Although some preferred embodiments have been described, many modifications and variations may be made thereto in the light of the above teachings. It is therefore to be understood that within the scope of the appended claims, the invention may be practiced otherwise than as specifically described.

I claim:

1. In connection with a catheter assembly comprising a dilation catheter having leading and trailing ends for dilating a stenosis in a blood vessel, said dilation catheter defining a longitudinal lumen extending from the leading end to the trailing end thereof and open at the leading and trailing ends, the dilation catheter further including a dilating member at the leading end, and a sheath defining a longitudinal bore through which said dilation catheter is inserted to define a blood intake gap between the outer surface of said dilation catheter and the bore, said sheath further including transverse bore means in fluid communication with the bore, the improvement comprising:
tube means for defining a continuous flowpath having one end connectable to said transverse bore means and another end connectable to the lumen at the trailing end of said dilation catheter, said tube means including at least one section of tubing to which blood pumping means is mountable, said tube means further including a pair of inflow and outflow sections of tubing connected to the bottom of a vertical blood reservoir, having a vent at the top, for passing blood into and out of the reservoir, respectively, said inflow section of tubing being connected to said at least one section of tubing to which the pumping means is mountable, wherein said tube means combined with said dilation catheter and said sheath provide a continuous blood flowpath connecting the blood intake gap, the sheath transverse bore means, the tube means, and the dilation catheter lumen to ensure normal blood flow by transporting a necessary amount of blood to the periphery of the stenosis through said flowpath.

2. The tube means of claim 1 which further comprises means disposed in the flowpath for storing blood.

3. The system of claim 1, further comprising a guiding catheter defining a lumen through which said dilation catheter is inserted, said blood intake gap being formed between the outer surface of said guiding catheter and said longitudinal bore through which said guiding catheter in inserted.

4. The system of claim 1 wherein said sheath includes:
a generally cylindrical hollow sheath body defining the longitudinal bore through which the dilation catheter is inserted to define the blood intake gap between the sheath bore and the dilation catheter,
a hub fluid-tightly engaged with a trailing portion of the sheath body, and
a transverse hollow protrusion forming said transverse bore means extending from the side of the hub and opening to communicate with the blood intake gap for passing blood therethrough.

5. A blood perfusion system comprising:
a dilation catheter having leading and trailing ends and defining a longitudinal lumen extending from the leading end to the trailing end and open at the leading and trailing ends, the dilation catheter further including a dilating member at the leading end,
a sheath having leading and trailing ends and defining a longitudinal bore through which said dilation catheter is inserted to define a blood intake gap between the outer surface of said dilation catheter and the bore, said sheath further including transverse bore means in fluid communication with the bore,
tube means for defining a continuous flowpath having one end connected to said transverse bore means and another end connected to the lumen at the trailing end of said dilation catheter, said tube means further including a vertical blood reservoir having a vent at the top, a first section of tubing to which blood pumping means is mountable, and a pair of inflow and outflow sections of tubing connected to the bottom of said vertical blood reservoir for passing blood into and out of the reservoir, respectively, said inflow section of tubing being connected to said first section of tubing, and
blood pumping means mounted to said first section of tubing for pumping blood therethrough,
whereby when said sheath having said dilation catheter inserted therein is set in a blood vessel, blood is taken into the blood intake gap in said sheath, passed through the sheath transverse bore means, said tube means, and the dilation catheter lumen, and fed back to the blood vessel through the open leading end of said dilation catheter.

6. The system of claim 5 which further comprises means inserted in the flowpath of said tube means for storing blood.

7. The system of claim 5 wherein said sheath further includes a valve body mounted at the trailing end thereof.

8. The system of claim 3 wherein said sheath includes:
a generally cylindrical hollow sheath body defining the longitudinal bore through which the guiding catheter is inserted to define the blood intake gap between the sheath bore and the guiding catheter,
a hub fluid-tightly engaged with a trailing portion of the sheath body, and
a transverse hollow protrusion forming said transverse bore means extending from the side of the hub and opening to communicate with the blood intake gap for passing blood therethrough.

9. The system of claim 5, further comprising a cock between said blood reservoir and the trailing end opening of the dilation catheter.

10. A blood perfusion system comprising:
a dilation catheter having leading and trailing ends and defining a longitudinal lumen extending from the leading end of the trailing end and open at the leading and trailing ends, the dilation catheter further including a dilating member at the leading end,
a guiding catheter defining a lumen through which said dilation carrier is inserted,
a sheath having leading and trailing ends and defining a longitudinal bore through which said guiding catheter having said dilation catheter received therein is inserted to define a blood intake gap between the outer surface of said guiding catheter and the bore, said sheath further including transverse bore means in fluid communication with the bore,
tube means for defining a continuous flowpath having one end connected to said transverse bore means and another end connected to the lumen at the trailing end of said dilation catheter, said tube means further including a vertical blood reservoir having a vent at the top, a first section of tubing to which blood pumping is mountable, and a pair of inflow and outflow sections of tubing connected to the bottom of said vertical blood reservoir for passing blood into and out of the reservoir, respectively, said inflow section of tubing being connected to said section of tubing to which said blood pumping means is mountable, and
blood pumping means mounted to said first section of tubing for pumping blood therethrough,
whereby when said sheath in which said guiding catheter with said dilation catheter received therein is inserted is set in a blood vessel, blood is taken into the blood intake gap in said sheath, passed through the sheath transverse bore means, said tube means, and the dilation catheter lumen, and fed back to the blood vessel through the open leading end of said dilation catheter.

11. The system of claim 10 which further comprises means inserted in the flowpath of said tube means for storing blood.

12. The system of claim 10 wherein said sheath further includes a valve body mounted at the trailing end thereof.

13. The system of claim 10 wherein said sheath includes:
a generally cylindrical hollow sheath body defining the longitudinal bore through which the guiding catheter is inserted to define the blood intake gap between the sheath bore and the guiding catheter, a hub fluid-tightly engaged with a trailing portion of the sheath body, and a transverse hollow protrusion forming said transverse bore means extending from the side of the hub and opening to communicate with the blood intake gap for passing blood therethrough.

14. The system of claim 10, further comprising a cock between said blood reservoir and the trailing end opening of the dilation catheter.

15. A method of blood perfusion comprising the steps of:

providing a dilation catheter having leading and trailing ends and defining a longitudinal lumen extending from the leading end to the trailing end and open at the leading and trailing ends, the dilation catheter further including a dilating member at the leading end, providing a sheath having leading and trailing ends and defining a longitudinal bore through which said dilation catheter is inserted to define a blood intake gap between the outer surface of said dilation catheter and the bore, said sheath further including transverse bore means in fluid communication with the bore, defining with a tubing a continuous flowpath having one end connected to said transverse bore means and another end connected to the lumen at the trailing end of said dilation catheter, providing said tube means with a vertical blood reservoir having a vent at the top, providing a first section of said tubing through which blood is pumped, and providing a pair of inflow and outflow sections of said tubing connected to the bottom of said vertical blood reservoir for passing blood into and out of the reservoir, respectively, said inflow section of tubing being connected to said first section of tubing, and bumping blood through said first section of tubing, whereby when said sheath having said dilation catheter inserted therein is set in a blood vessel, blood is taken into the blood intake gap in said sheath, passed through the sheath transverse bore means, said tubing, and the dilation catheter lumen, and fed back to the blood vessel through the open leading end of said dilation catheter.

* * * * *